US011213238B2

(12) United States Patent
Shastri et al.

(10) Patent No.: US 11,213,238 B2
(45) Date of Patent: Jan. 4, 2022

(54) CARDIAC HEALTH MONITORING DEVICE AND A METHOD THEREOF

(71) Applicant: IMEDRIX SYSTEMS PRIVATE LIMITED, Bangalore (IN)

(72) Inventors: Rajaram Shastri, Bangalore (IN); Nagesh Rangappan, Bangalore (IN); Venkatakrishna Araveti, Bangalore (IN); Niranjan Rayaprolu, Bangalore (IN); Srikanth Jadcherla, San Jose, CA (US); Kishore Ramasamy, Bangalore (IN); Lokesh Kumar Kata, Bangalore (IN)

(73) Assignee: IMEDRIX SYSTEMS PRIVATE LIMITED, Bangalore (IN)

( * ) Notice: Subject to any disclaimer, the term of this patent is extended or adjusted under 35 U.S.C. 154(b) by 34 days.

(21) Appl. No.: 16/466,006

(22) PCT Filed: Dec. 31, 2017

(86) PCT No.: PCT/IN2017/050630
§ 371 (c)(1),
(2) Date: May 31, 2019

(87) PCT Pub. No.: WO2018/122879
PCT Pub. Date: Jul. 5, 2018

(65) Prior Publication Data
US 2019/0290151 A1    Sep. 26, 2019

(30) Foreign Application Priority Data
Dec. 30, 2016    (IN) .............................. 201641045054

(51) Int. Cl.
*A61B 5/00* (2006.01)
*A61B 5/318* (2021.01)
(Continued)

(52) U.S. Cl.
CPC ............ *A61B 5/318* (2021.01); *A61B 5/0006* (2013.01); *A61B 5/7235* (2013.01); *G16H 10/60* (2018.01);
(Continued)

(58) Field of Classification Search
None
See application file for complete search history.

(56) References Cited

U.S. PATENT DOCUMENTS 9,248,294 B2 * 2/2016 Prinzen .................. A61N 1/371
9,339,202 B2 * 5/2016 Brockway ............ A61B 5/0015
(Continued)

OTHER PUBLICATIONS

Rahimpour, M., Asl, M. E., & Merati, M. R. (2016). ECG fiducial points extraction USING QRS morphology and ADAPTIVE windowing for Real-time ECG signal analysis. 2016 24th Iranian Conference on Electrical Engineering (ICEE). doi:10.1109/iraniancee.2016. 7585836 (Year: 2016).*
(Continued)

*Primary Examiner* — Gary Jackson
*Assistant Examiner* — Anant A Gupta
(74) *Attorney, Agent, or Firm* — Intellectual Property Law Group LLP

(57) ABSTRACT

The various embodiments of the present invention disclose a stand-alone, scalable cardiac health monitoring device for 1-6-12 lead ECG data acquisition and a method of working thereof. The method of monitoring cardiac health condition of a patient comprises of receiving, by a cardiac monitoring device, an electrocardiograph (ECG) input data signals from at least two electrodes attached to the patient, performing, a quality check on acquiring the ECG input data signals, processing the acquired ECG input data signals, encrypting the processed ECG input data signals and transmitting the encrypted ECG signals to one or more external user devices over a wireless communication interface. The acquiring the
(Continued)

ECG input data signals comprises of integrating a closed loop Right Leg Drive (RLD) as a shield drive and a cable/electrode shield to reduce noise coupling to the ECG input data signals.

7 Claims, 6 Drawing Sheets

(51) Int. Cl.
    *G16H 10/60*     (2018.01)
    *G16H 50/30*     (2018.01)
    *G16H 40/63*     (2018.01)

(52) U.S. Cl.
    CPC .......... *G16H 50/30* (2018.01); *A61B 2562/18* (2013.01); *A61B 2562/182* (2013.01); *G16H 40/63* (2018.01)

(56) References Cited

U.S. PATENT DOCUMENTS

| | | | |
|---|---|---|---|
| 9,763,097 B2* | 9/2017 | Robinson | H04L 63/0853 |
| 9,763,590 B1* | 9/2017 | Rood | A61N 1/04 |
| 9,974,492 B1* | 5/2018 | Dicks | G16H 40/63 |
| 2007/0032733 A1* | 2/2007 | Burton | A61B 5/4812 600/509 |
| 2011/0270112 A1* | 11/2011 | Manera | A61B 5/349 600/523 |
| 2013/0184600 A1* | 7/2013 | Tan | A61B 5/4836 600/518 |
| 2014/0081118 A1 | 3/2014 | Reinhold et al. | |
| 2014/0107457 A1* | 4/2014 | Nathan | A61B 5/0006 600/386 |
| 2015/0072326 A1* | 3/2015 | Mauri | A61B 5/6804 434/247 |
| 2015/0148634 A1* | 5/2015 | Garudadri | A61B 5/087 600/323 |
| 2015/0223712 A1* | 8/2015 | Govari | G01R 33/5673 600/411 |
| 2016/0302674 A1 | 10/2016 | Moyer et al. | |
| 2017/0039568 A1* | 2/2017 | Tunnell | G06F 21/33 |
| 2017/0143272 A1* | 5/2017 | Brouse | A61B 5/02416 |
| 2018/0116537 A1* | 5/2018 | Sullivan | A61B 5/6802 |
| 2019/0350535 A1* | 11/2019 | Zhao | A61B 5/02055 |

OTHER PUBLICATIONS

International Search Report, dated Apr. 10, 2018 for corresponding International Application No. PCT/IN2017/050630.
Written Opinion of the ISA, dated Apr. 10, 2018 for corresponding International Application No. PCT/IN2017/050630.

* cited by examiner

CARDIAC HEALTH MONITORING DEVICE AND A METHOD THEREOF

RELATED APPLICATION

The present invention claims benefit of the Indian Provisional Application No. 201641045054 titled "CARDIAC HEALTH MONITORING DEVICE" by iMEDRIX SYSTEMS PRIVATE LIMITED, filed on 30 Dec. 2016, which is herein incorporated in its entirety by reference for all purposes.

FIELD OF THE INVENTION

The present invention generally to Electrocardiograph (ECG) monitoring of patients and particularly relates to a self-contained, portable device for monitoring and recording of ECG data.

BACKGROUND OF THE INVENTION

It is well known that expansions and contractions of the cardiac muscle produce electrical signals. These signals, which can be sensed by properly positioning electrodes on the surface of a person's skin, are most frequently called electro cardiac or ECG signals. The prior art has suggested various devices for monitoring ECG signals since, by analyzing these signals, an indication is provided as to the normal or abnormal condition of the monitored-heart.

The CVD condition is spreading rapidly and is affecting not only the aged people but also the people in early ages as well. The wide-spread and massive screening and prevention is the only way before it become too late. Hence a quick and accurate measurement of the ECG is the need of the hour. The device used should provide accurate and clinically acceptable data. It should also have the flexibility to support multiple leads and allow measurement of related parameters, which enable doctors to understand realistic conditions of the patient's health and health habits.

The prior art discloses numerous devices wherein ECG data or the like is monitored and/or transmitted from a patient to a particular doctor's office or health service center. However, these conventional devices are generally 12-lead devices or bed side monitoring machines predominantly used in hospital conditions only. The other ECG measuring devices, which allow handheld measurements, are either a smart phone accessory or have limitations in measuring a single lead ECG and does not allow to measure other clinically useful parameters.
Further the conventional ECG devices which produce clinical grade accuracy are still confined to Hospital-walls. These devices which can be used outside the hospital set-up, such as Home-care, public-screening and Telemedicine application are limited to either heart-rate monitoring or Atrial fibrillation detection. Though some device has connectivity, it still requires certified technicians to operate, which seriously limit the usability and scalability to reach larger population.

In view of the foregoing, there exists the need for a ECG monitoring device, which can be used universally, across various usage environments including remote monitoring and can be used seamlessly with minimal training requirements and still producing clinical grade accuracy of ECG traces

SUMMARY OF THE INVENTION

The various embodiments of the present invention disclose a cardiac health monitoring system and a non-invasive method of measuring cardiac health parameters of a user using Electrocardiograph (ECG) and to provide expert-feedback. The cardiac health parameters thus measured is then fed to an analysis system, which analyzes the input data and provides opinions and feedback regarding the cardiac health, specific to each individual. The cloud based portal also serves as a data repository, creating a Personal Health Record (PHR) System.

According to an embodiment of the present invention, the method of monitoring cardiac health condition of a patient comprises of receiving by the cardiac monitoring device an electrocardiograph (ECG) input signals from at least two electrodes attached to the patient, performing a quality check on acquiring the input ECG data signals, processing the acquired ECG input data signals, encrypting the processed ECG input signals and transmitting the encrypted ECG signals to one or more external user devices over a wireless communication interface. Here processing the ECG signals comprises of minimizing a signal to noise ratio by integrating a Right Leg Drive (RLD) derived using an average of input voltages obtained from the right arm (RA), left leg (LL) and right leg (RL) electrodes.

According to an embodiment of the present invention, the at least two electrodes is one of a finger electrode, a clamp electrode and a standard 12 lead electrode. The finger electrodes are uniquely designed to provide better Signal to Noise Ratio (SNR). The surface roughness and the electrode plating reduce the contact noise, allows uniform-pressure on the contact surface and increases conductivity. Further, the electrodes support more than 1 Lakh touches without any degradation in the signal quality.

According to an embodiment of the present invention, a closed loop RLD is used as a shield drive and cable shield to derive the body potential by monitoring changes in the body-potential and drive proper DC-voltage to maintain the potential closer to mid-scale range, there-by avoiding input saturation.

According to an embodiment of the present invention, performing the quality check of the input ECG data signals comprises of verifying, by a signal filtering unit, if a lead check is correct or not by checking at least one of a lead contact error, a lead sequencing error and an artefact noise in the ECG data signals, analyzing the lead check data in both frequency domain and time domain, generating a score indicative of the correctness of the lead check data and transmitting a message indicating the correctness and accuracy of the captured ECG data signals to a remote user. The context-aware (different lead conditions, finger, 6-lead and 12-lead) filters optimize its parameters dynamically and also based on the noise level present in the signal, thereby providing clinical grade ECG in all usage conditions.

According to an embodiment of the present invention, performing signal quality analysis further comprises of detect the presence of Flat Line, Sudden high impulses, Baseline Noise, Motion Artifacts and Muscle Artefacts on each lead which is being used to acquire signals. The quality analysis is performed using both Time and Frequency domains. A Power Spectral Analysis is performed at certain range of frequencies using which, the cardiac health monitoring device will detect the amount of various noise present in an ECG Signal.

According to an embodiment of the present invention, the amount of power at specific frequency component and it's variation across the signal determines the input signal characteristics. The HR variations, and correlations are used to analyze the signal quality in time domain. Using an efficient and robust rule engine scores are allocated to each lead (using time domain and frequency domain analysis). When multiple leads are used for acquisition, scores from each lead are combined and total scoring is derived.

According to an embodiment of the present invention, the Signal Quality Score associated with each signal enables to decide whether the recorded ECG Signal is good for clinical analysis or not and also provide details on the type and amount of noise present in the input signal for every lead. This in turn allows to provide feedback to remote operator.

According to an embodiment of the present invention, detecting the lead errors further comprises of analyzing QRS Balance, QRS Axis and P Wave orientation on every lead. Further Peak to Peak QRS magnitude and T-wave amplitude are used to determine whether the electrode-skin contact is good or not. The area inscribed by QRS complexes is employed in determining the proper placement of chest leads.

According to an embodiment of the present invention, capturing the input ECG data signals comprises of performing an auto-tuning procedure for capturing a lead location, by using a history data and calibrating the lead positions by prompting the user to locate correct lead positions dynamically.

According to an embodiment of the present invention, capturing the input ECG data signals further comprises of initiating an auto-calibration procedure before capturing each inputs ECG data signals. The auto-calibration procedure comprises of analyzing the input ECG data signals, comparing the ECG data signals with a reference signal for amplitude, frequency and morphology correctness and tuning one or more scaling factors based on the comparison.

According to an embodiment of the present invention, the processed ECG input signals are encrypted by combining a device's unique number, an operator ID, patients Unique Health Identification (UHID) code and a location code.

According to an embodiment of the present invention, the method further comprises of performing by the cardiac monitoring device a respiration measurement, body-impedance measurement, photo-plethysmography signals measurement and blood pressure measurement, thereby providing a combined diagnostic of ECG, respiration and body-impedance parameters of the patient for vital parameter analysis.

According to an embodiment of the present invention, the method further comprises of activating by the cardiac monitoring device a self-lock mechanism, thereby entering to a self-lock mode and becomes non-functional. The device can be re-activated only after appropriate authorization by authorized person using unique commands.

The method of claim 1, wherein the by a cardiac health monitoring device is a battery operated, handheld and a resilient (works equally good at hospital, home and harsh open-air conditions) mobile communication device.

Embodiments herein further disclose a cardiac health monitoring device, where the device comprises a battery powered ECG monitor adapted to receive ECG input signals from two or more electrodes attached to a patient, a data acquisition and shield drive selection unit adapted for acquiring the input ECG data signals, performing AC coupling of the acquired ECG data signals and providing an RLD drive and integrating the ECG signals to have an average which is equal to ADCs mid-range; where RLD drive is a continuous average of RA, LA and LL data obtained from the two or more electrodes, a signal filtering unit comprising a high pass hardware filter adapted for removing the half-cell DC value to enable the channels to work with the AC components, a configurable digital decimation filters adapted for band-limiting the input ECG data signals to a preset frequency and segregating ECG signals from lead-check, pacemaker identification pulse and impedance measurement signals and related artefacts, one or more signal processing units for processing the ECG input signals, a controller unit adapted for auto-tuning of the processed ECG signals and interfacing with a communication unit for transmitting the encrypted ECG signals to one or more external user devices.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
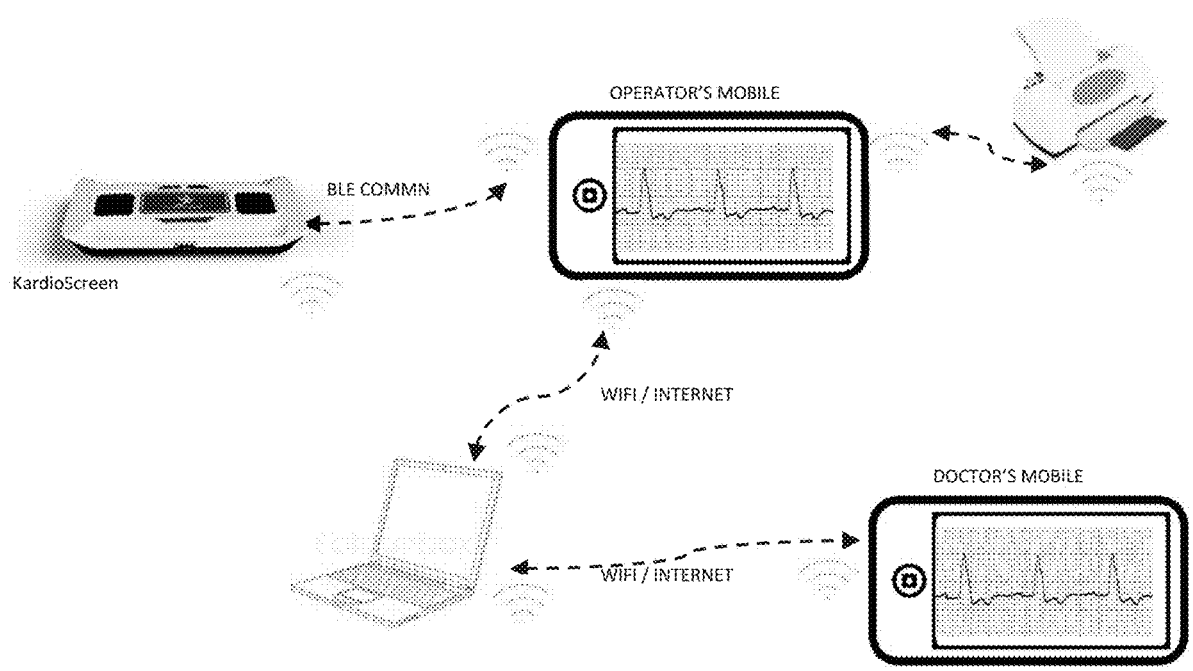
FIG. 1 is a scenario diagram illustrating working environment of the cardiac health monitoring device, according to an embodiment of the present invention.

Although specific features of the present invention are shown in some drawings and not in others, this is done for convenience only as each feature may be combined with any or all of the other features in accordance with the present invention.

DESCRIPTION OF THE INVENTION

The various embodiments of the present invention disclose a cardiac health monitoring system and a non-invasive method of measuring cardiac health parameters of a user using Electrocardiograph (ECG) and to provide expert-feedback. The cardiac health parameters thus measured is then fed to an analysis system, which analyzes the input data and provides opinions and feedback regarding the cardiac health, specific to each individual. The cloud based portal also serves as a data repository, creating a Personal Health Record (PHR) System.

The cardiac health monitoring device comprises at least two electrodes provided on the handheld device for receiving an ECG input from a user, a data acquisition and shield drive selection unit, one or more signal converters/processors, a signal filtering unit, a controller to generate an ECG recording from the processed ECG signals and a communication unit for transmitting the ECG recording to one or more user devices. The device further comprises one or more accessories, for instance, clamps attached to the device for capturing ECG inputs from the users.

According to an embodiment of the present invention, the cardiac health monitoring device herein is a scalable device employing a 1-6-12-lead ECG acquisition. The ECG thus acquired is then transmitted to one or more remote devices, or a cloud server for further health analysis.

According to an embodiment of the present invention, the cardiac health monitoring device further processes the recorded ECG reading for further health analysis of the user. The cardiac health monitoring device herein is portable, battery operated, handheld/pocket sized and rugged mobile communication device adapted for working in different environments like Hospitals, Point-of-care, health screening camps, TMO, remote/home monitoring systems and the like. Further the cardiac health monitoring device disclosed herein measures the signal without the requirement of any gel, as compared with the conventional ECG monitors. the cardiac monitoring device is a standalone device capable of ECG acquisition and to transmit the captured data directly to smart-phone, cloud etc.

The cardiac health monitoring device can be used for recording ECGs of the patients in both supine and non-supine positions. The finger electrode design, clamp electrodes and the standard 12 lead electrodes surface finish of the cardiac monitoring device and the unique shield-drive methods disclosed herein greatly reduce the baseline-wander noise, increase the signal noise ratio and provides greater data accuracy, for different skin types and age groups, making ease of use with clinical data accuracy.

The device herein uses a unique encryption method for storing the ECG data locally at the device. Further the device herein, synchronize with cloud servers for storing of ECG data at periodic intervals for enhanced security, thereby preventing any tampering of the data. The cardiac monitoring device herein is a battery-operated device, adapted to work in conjunction with any mobile phone or tablet and can also work as autonomous device, capable of sending the ECG data directly to a cloud server.

According to an embodiment of the present invention, the methods employed by the device for de-noising, to measure quality of signal acquisition in real-time, auto-calibration and auto tuning methods enriches the device usage, allowing it to be used in different environments and application areas. Further, the device herein is also adapted to measures respiration and impedance measurement, thereby providing a combined diagnostic of ECG, Respiration and body-impedance parameters, for further processing and analyzing.

According to an embodiment of the present invention, the cardiac health monitoring device herein is adapted to measure additional health parameters like peripheral capillary oxygen saturation (SPO2), blood pressure and the like, making it a complete health diagnostic unit.

According to an embodiment herein, the device is adapted to check the lead contact error, lead sequencing error or any artefact noise in the signal and further analyze the data in both frequency and time domain. Various scores are generated and indicated to user on the correctness and accuracy of the signal being captured. The device also alerts the user if there are any errors or noise while placing the leads or capturing the signal.

FIG. 1 is a scenario diagram illustrating a working environment of the cardiac health monitoring device, according to an embodiment of the present invention. The system comprises of a cardiac health monitoring device in communication with one or more external user devices such as a laptop, tablet, mobile phone or the like. The cardiac monitoring device transmits data through wireless communication methods, which can function as a companion device for any mobile device or can directly transmit data to cloud, operating as an autonomous device too.

The cardiac health monitoring device herein provides for 1-6-12 leads of ECG data signal capture. The 1-lead and 6-lead configurations can be used, but not limited to, at home for self-monitoring and/or symptomatic, Point-of-Care and Primary Screening application and the 12-lead configuration can be used for Extended screening, hospitals, emergency vehicles and the like.

The cardiac health monitoring device herein supports an auto-calibration functionality, through which device is calibrated before every ECG is recorded. A known signal is fed into the device and analyzed for amplitude, frequency and morphology. The device is calibrated and scaling factors are tuned based on the comparison results. The procedure makes sure that every ECG recorded using the device is calibrated.

The finger electrodes provided are uniquely designed to provide better SNR. The surface roughness and the electrode plating reduce the contact noise, allows uniform-pressure on the contact surface and increases conductivity. These electrodes support more than 1 Lakh touches without any degradation in the signal quality. Further a Right Leg Drive (RLD), derived using the average of input voltages obtained from the right arm, left leg and right leg (RA, LL and RL) electrodes, is integrated to minimize the noise. Thus, the closed loop RLD is used to drive the body potential, by continuously monitoring the changes in the body-potential and drive proper DC-voltage to maintain the potential closer to mid-scale range, there-by avoiding input saturation, and always operating in linear range. The RLD drive is used as shield drive and cable shield is connected to it. This technique helps to minimize the external noise coupling into the ECG signals.

The inputs are AC coupled, with the lower cut-off frequency of 0.05 Hz. Due to this very low frequency start-up time of the channel could be very long and inputs can cause ringing effect. Introduction of fast settling switch at the inputs avoids all these issues, which dynamically lowers the cut-off frequency starting from 10 Hz, 5 Hz to 0.7 Hz and finally 0.05 Hz. Very high input impedance (1 GΩ) of the input stage, reduces the input coupling noise, uniquely selected input stage provides high input impedance on all the differential channels with great extent of matching between the channels.

The ECG Scores are computed on the acquired data, to check the quality of the acquisition. The captured data is encrypted and stored before sending over the wireless link. The encryption method used herein is by combining the device's unique number, patients UHID and location code, thereby maintaining the data integrity.

The device herein synchronizes with a companion device or with a Cloud-server, at periodic intervals, for instance, at-least once in two days for data transfer. Failure to do so, will trigger a self-lock mechanism, where the cardiac monitoring device will get locked and becomes non-functional. Further the device can be re-activated only after requisite authentication. The unique re-activation process is enabled through a wired communication, through an authorized person using authorized commands.

According to an embodiment of the present invention, device herein enables impedance and respiration measurement by driving a very low signal into the body and measuring it. IQ modulation techniques are used, which is less susceptible for the physiological variations. 31.25 Khz AC signal of programmable drive strength of 5 to 20 μA, is injected in to the body. The received signal is demodulated and both amplitude and phase information are extracted. The amplitude and phase variations are then compared with ECG plots to infer respiration and impedance details.

The cardiac monitoring device communicates with the one or more external devices over a wired or wireless communication medium, comprising, but not limited to, Wi-Fi, Bluetooth, Infrared and so on. The user can place the thumb on the finger electrodes provided on the device, which takes the lead-1 measurements, which is predominantly used for detecting the cardiac conditions.

Figure 2:
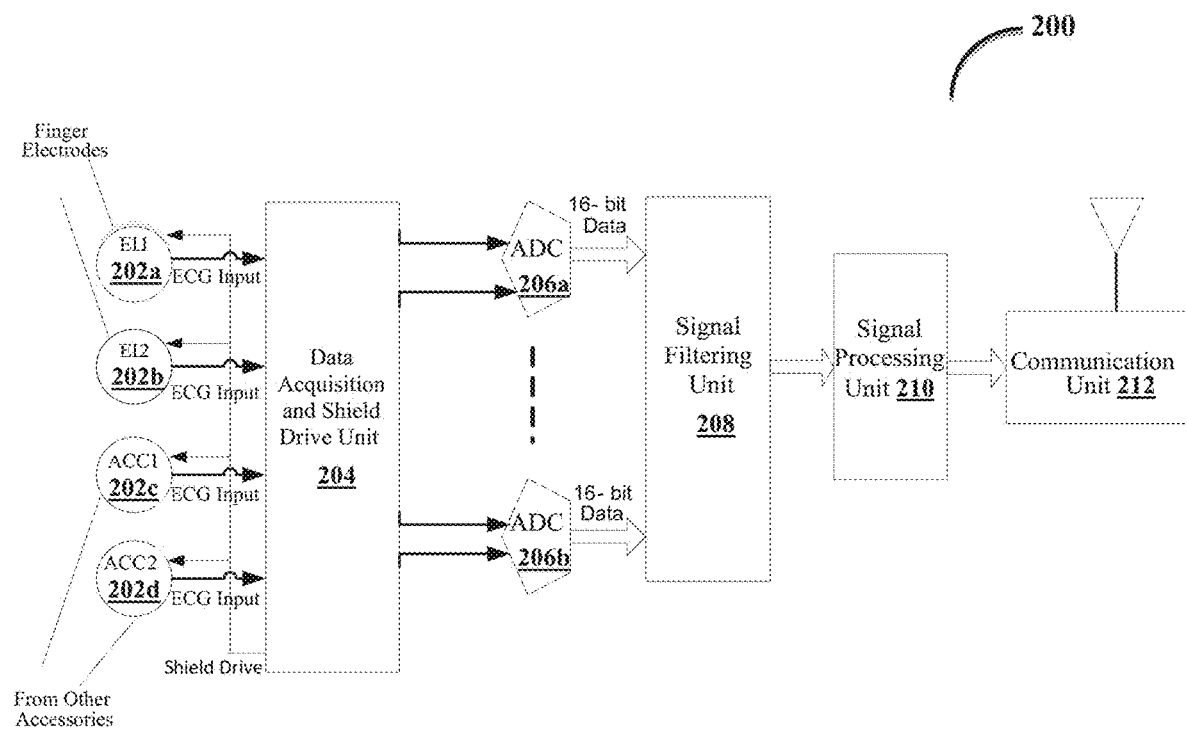
FIG. 2 is a block diagram illustrating the functional components of the cardiac health monitoring device, according to an embodiment of the present invention.

FIG. 2 is a block diagram illustrating the functional components of a cardiac health monitoring device 200, according to an embodiment of the present invention. The cardiac health monitoring device 200 comprises at least two electrodes 202a, 202b for receiving an input ECG data signals from a patient, a data acquisition and shield drive unit 204, one or more signal converters 206, a signal filtering unit 208, a signal processing unit 210 to generate an ECG recording from the processed ECG signals and a communication unit 212 for transmitting the ECG recordings to one or more remote user devices.

According to FIG. 2, the inputs are fed to the device either through both the electrodes (EL1 and EL2) 202a and 202b or through the accessory 202c and 202d (ACC1/ACC2) attached to the device. The data acquisition and shield drive unit 204 acquires the input ECG data signal, performs the AC coupling and filtering of the input data signal. Further the data acquisition and shield drive unit 204 provides a very high input impedance (>1 GΩ) for the input signals, which is essential for capturing any bio-potential signals.

According to an embodiment herein, the data acquisition and shield drive unit 204 also provides an RLD drive, which is a continuous average of RA, LA and LL and integrates the signal to have an average which is equal to signal converters (ADCs) mid-range. Due to this, the input can take very high common mode inputs while maintaining the ADCs 206a and 206b dynamic range intact. Further to data acquisition, the signals are digitized and a high-resolution ADC is used for sampling and digitization. Over sampling and decimation techniques are done to further reduce the noise on the signals. The signal filtering unit 208 comprises high pass hardware filter which removes the half-cell DC value to enable the channels to work with the AC components only. These equally matched filters remove the common mode DC signals. The signal filtering unit 208 comprises configurable digital decimation filters adapted to band-limit the signal to the desired frequency. These filters segregate ECG signal from lead-check, pacemaker identification pulse and impedance measurement signals and their artefacts. The signal filtering unit 208 checks for lead contact error, lead sequencing error or any artefact noise in the signal. The signal filtering unit 208 analyses the data in both frequency and time domain. Various scores are generated and indicated to user on the correctness and accuracy of the signal being captured. The signal filtering unit 208 also alerts the user if there are any errors or noise while placing the leads or capturing the signal.

The signal processing unit 210 receives the digitized data, and stores in the device memory for further processing. Signal quality estimation is carried out on the input data stream and signal is monitored for proper capture and an Error message is sent out if the signal quality is below the threshold. The signal processing unit 210 further performs the calibration and auto tuning process. The signal processing unit 210 also interfaces with communication module to send data either to a companion device or directly to cloud. Here the data is encrypted and Stored before sending over secure wireless link. A unique encryption method is used by combining the device's unique number, operator ID, patients UHID and location code, thus maintaining the data integrity.

The signal processing unit 210 synchronizes with the cloud server periodically over a wireless communication medium for transfer of the data signals. Failing to do so triggers the auto-lock mechanism, where the device gets into a self-lock mode, and only authorized person with the authorized commands can un-lock the device. This tamper proofing method maintains data integrity and authenticity of the cardiac monitoring device herein.

Figure 3:
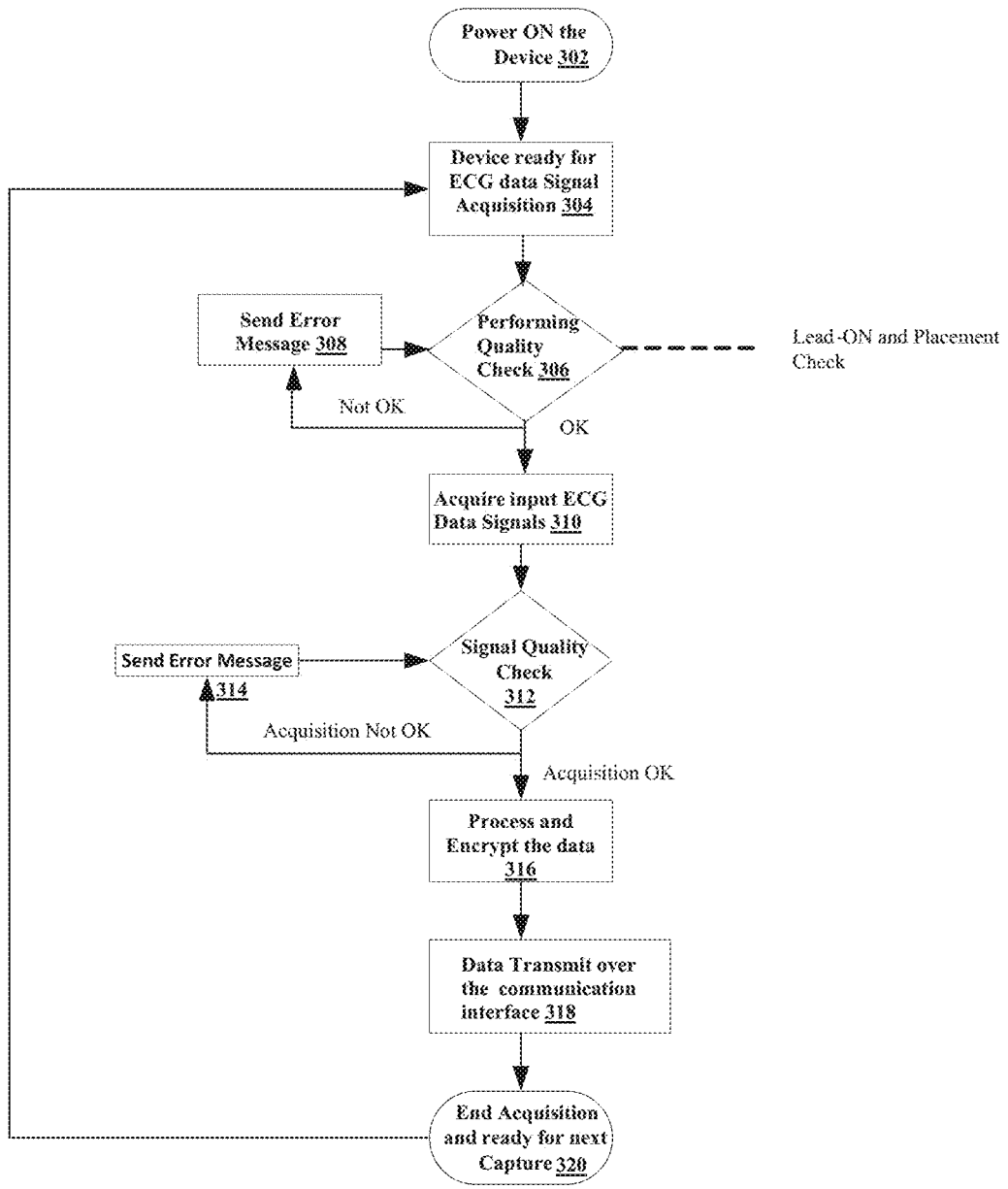
FIG. 3 is a flow diagram illustrating a method for monitoring cardiac health condition of a patient, according to an embodiment of the present invention.

FIG. 3 is a flow diagram illustrating a method for monitoring cardiac health condition of a patent, according to an embodiment of the present invention. At step 302, activate the cardiac monitoring device by powering on and enable the device for cardiac signal acquisition at step 304. At step 306, perform a lead ON and thumb placement check to receive ECG input from the user. If the lead check is not correct, then send an error message to the user at step 308. At step 310, acquire ECG input signal if the lead check is correct and performs a quality check of the ECG input signal at step 312. If the ECG input signal acquisition is not correct, then send an error message at 314. Further, at step 316, encrypt and store the ECG data if the signal acquisition is correct. Further at step 318, the acquired ECG input signal is processes and transmit the processes ECG signals to the one or more external user devices over a wireless communication interface and terminate the ECG input signal acquisition at step 320.

Figure 4A:
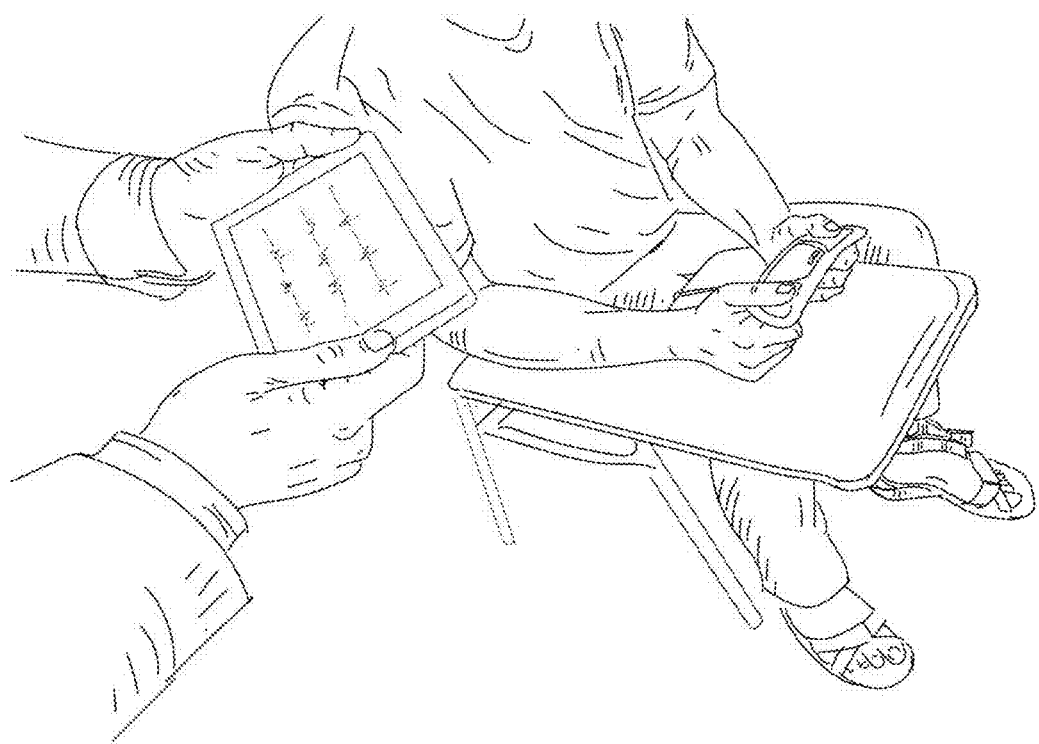
FIG. 4a-4c are schematic diagrams illustrating example scenarios of measuring ECG using the cardiac health monitoring device, according to an embodiment of the present invention.
Figure 4B:
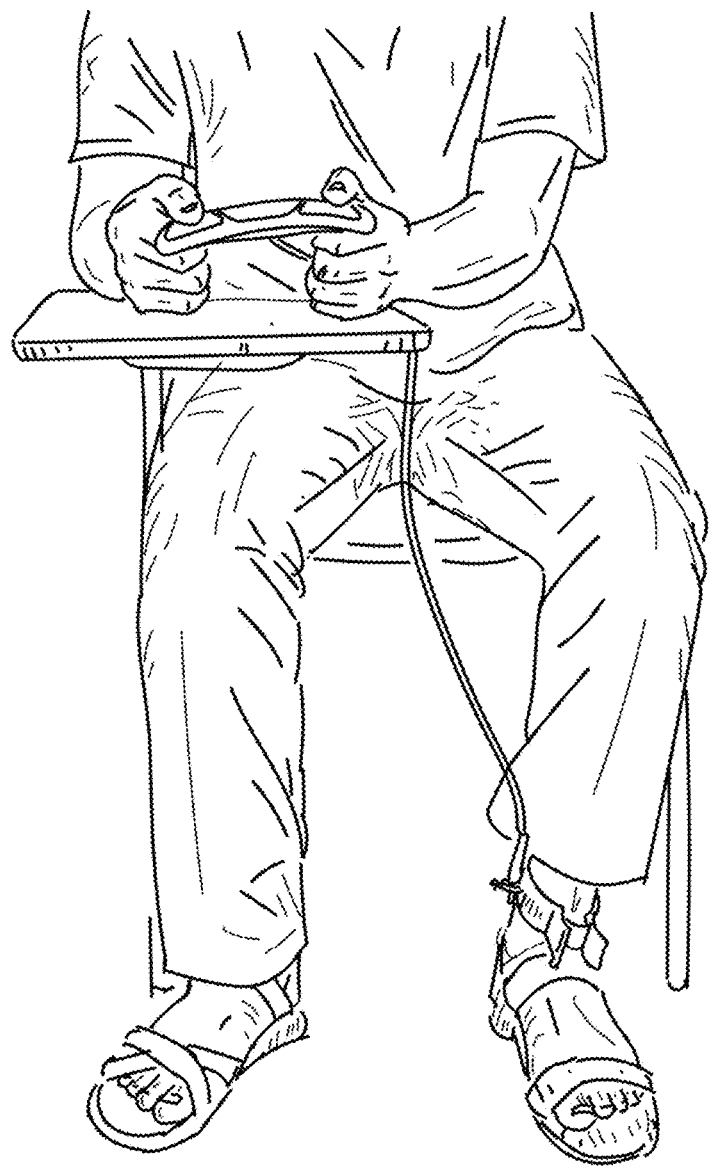
Figure 4C:
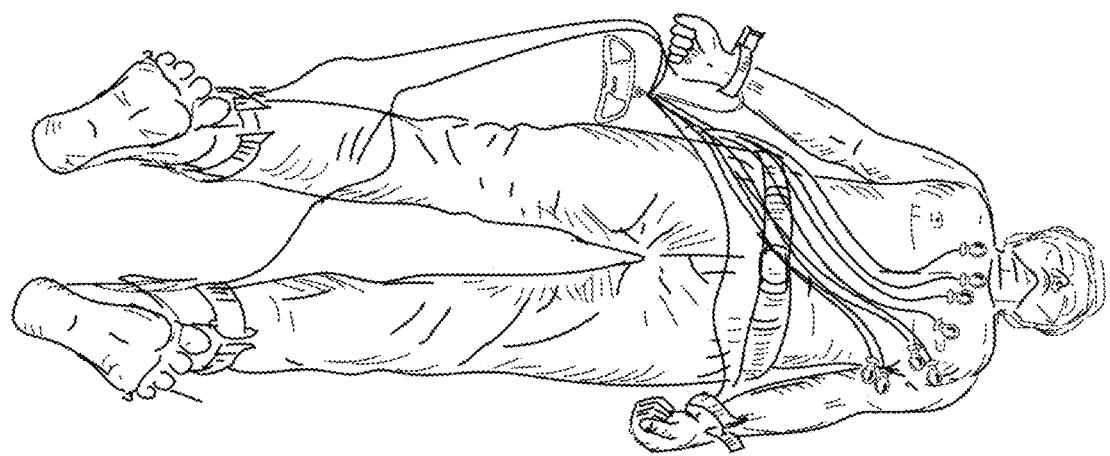

FIG. 4a-4c is a schematic representation illustrating example scenarios of measuring ECG using the cardiac monitoring device, according to an embodiment of the present invention. A person, holds the cardiac monitoring device using his hand with thumbs placed on finger electrodes, can take Lead-1 measurement, which is predominantly used for detecting the cardiac health condition, as shown in FIG. 4a.

The cardiac monitoring device provides a 6 lead ECG input signal data, when the user places both the thumbs on the finger electrodes and the cable accessory clamped to the left leg of the user as shown in FIG. 4b. The 6-lead measurement thus obtained can be used for complete Arrhythmia monitoring, Conduction related issues and ST segment changes and the like. The 6-Lead measurement is most preferred mode for home-monitoring, screening camps and quick screening at Point-of-care.

Further using 12L-Cable accessory, complete 12-lead measurements can be taken using the cardiac monitoring device as shown in FIG. 4c, where the person is lying in a supine position. The procedure makes use of history data, and calibrate the lead placement by prompting the user to locate correct positions, dynamically. The input data is used to calibrate against history data, till correct location is identified. The auto-tuning lead location procedure as disclosed herein allows paramedics and semi-skilled personal to place the 12-lead cable into correct position for 12-lead ECG reading, which otherwise would have been possible only by trained technicians.

The finger electrodes of the cardiac monitoring device are uniquely designed to provide better SNR. The surface roughness and the electrode plating reduce the contact noise, allows uniform-pressure on the contact surface and increases conductivity. Electrodes support more than 1 Lakh touches without any degradation in the signal quality.

According to an embodiment of the present invention, the RLD-drive, derived using an average of input voltages (RA, LL and RL), is integrated to minimize the noise. Thus, the closed loop RLD-drive is used to drive the body potential, by continuously monitoring the changes in the body-potential and drive proper DC-voltage to maintain the potential closer to mid-scale range, there-by avoiding input saturation, and always operating in linear range. The RLD drive is used as shield drive and cable shield is connected to it. This technique helps to minimize the external noise coupling into the ECG signals.

According to an embodiment of the present invention, the inputs are AC coupled, with the lower cut-off frequency of 0.05 Hz. Due to this very low frequency, start-up time of the channel could be very long and inputs can cause ringing effect. Introduction of fast settling switch at the inputs avoids all these issues, which dynamically lowers the cut-off frequency starting from 10 Hz, 5 Hz to 0.7 Hz and finally 0.05 Hz. Very High input impedance (<1 G$\Omega$) of the input stage, reduces the input coupling noise, uniquely selected input stage provides high input impedance on all the differential channels with great extent of matching between the channels.

Ease of use and self-usable features such as Autonomous acquisition, dynamic lead placement method and unique auto-calibration methods, allow the device to be used at home for a complete cardiac diagnostic tool. The de-noising method used to extract ECG signals from various external noises optimizes itself dynamically based on input noise, because noise levels and conditions vary based on the device usage (1-lead, 6-lead, 12-lead etc) and environment. Thus, making accurate and clinical grade ECG is extracted every time.

The present embodiments have been described with reference to specific example embodiments; it will be evident that various modifications and changes may be made to these embodiments without departing from the broader spirit and scope of the various embodiments. Furthermore, the various devices, modules, and the like described herein may be enabled and operated using hardware circuitry, for example, complementary metal oxide semiconductor based logic circuitry, firmware, software and/or any combination of hardware, firmware, and/or software embodied in a machine readable medium. Although the embodiments herein are described with various specific embodiments, it will be obvious for a person skilled in the art to practice the invention with modifications.

We claim:

1. A method of monitoring cardiac health condition of a patient, the method comprising steps of:
    receiving, by a cardiac monitoring device, an electrocardiograph (ECG) input data signals from at least two electrodes attached to the patient, wherein the at least two electrodes is one of a finger electrode, a clamp electrode and a standard 12 lead electrode;
    performing, by the cardiac monitoring device, a quality check on acquiring the ECG input data signals, wherein performing the quality check on acquiring the ECG input data signals based on a lead check comprises of:
        determining whether electrode-skin contact is established or not by checking Peak to Peak QRS magnitude and T-wave amplitude by comparing the QRS magnitude and T-wave amplitude to a first threshold value, and
        determining area inscribed by QRS complexes to determine placement of leads by comparing the determined area to a second threshold value;
    processing, by the cardiac monitoring device, the acquired ECG input data signals;
    encrypting the processed ECG input data signals; and
    transmitting the encrypted ECG signals to one or more external user devices over a wireless communication interface;
    wherein acquiring the ECG input data signals comprises of:
        integrating a closed loop Right Leg Drive (RLD) as a shield drive and a cable/electrode shield to reduce noise coupling to the ECG input data signals, thereby increasing a Signal to Noise Ratio (SNR) of the acquired ECG input data signals.

2. The method of claim 1, wherein the RLD is derived using an average of input voltages obtained from a right arm (RA), a left leg (LL) and a right leg (RL) electrodes.

3. The method of claim 1, wherein performing the quality check of the ECG input data signals comprises of:
    verifying, by a signal filtering unit, if the lead check is correct or not by checking at least one of a lead contact error, a lead sequencing error and an artefact noise in the ECG input data signals;
    analyzing the lead check data in both frequency domain and time domain;
    generating a score indicative of a correctness of the lead check data; and
    transmitting a message indicating the correctness and accuracy of the captured ECG data signals to a remote user.

4. The method of claim 3, wherein verifying the lead check comprises of detecting presence of one or more of flat lines, sudden high impulses, baseline noise, motion Artifacts and muscle artefacts on the at least two electrodes from which the ECG input data signals is acquired.

5. The method of claim 1, wherein capturing the input ECG data signals further comprises of performing an auto-tuning procedure for capturing a lead location, by using a history data and calibrating the lead positions by prompting a user to locate correct lead positions dynamically.

6. The method of claim 1, wherein capturing the input ECG data signals further comprises of:
    initiating an auto-calibration procedure before capturing each inputs ECG data signals, wherein the auto-calibration procedure comprises of:
    analyzing the input ECG data signals;
    comparing the input ECG data signals with a reference signals to determine a difference in amplitude, frequency and morphology between the input ECG data signals and the reference signals; and
    tuning one or more scaling factors based on the comparison.

7. The method of claim 1, wherein the processed input ECG data signals are encrypted by combining a device's unique number, an operator ID, patients Unique Health Identification (UHID) code, a location code.

* * * * *